(12) United States Patent
Bell et al.

(10) Patent No.: US 9,719,028 B2
(45) Date of Patent: Aug. 1, 2017

(54) METHOD FOR PREDICTING ADSORBENT PERFORMANCE

(75) Inventors: Alexis T. Bell, Berkeley, CA (US); Manju Sharma, Berkeley, CA (US); Berend Smit, Berkeley, CA (US); Bi-Zeng Zhan, Albany, CA (US); Alice Zunqing He, San Rafael, CA (US)

(73) Assignees: THE REGENTS OF THE UNIVERSITY OF CALIFORNIA, Oakland, CA (US); CHEVRON U.S.A. INC., San Ramon, CA (US)

( * ) Notice: Subject to any disclaimer, the term of this patent is extended or adjusted under 35 U.S.C. 154(b) by 732 days.

(21) Appl. No.: 13/416,922

(22) Filed: Mar. 9, 2012

(65) Prior Publication Data

US 2012/0232863 A1    Sep. 13, 2012

Related U.S. Application Data

(60) Provisional application No. 61/450,780, filed on Mar. 9, 2011.

(51) Int. Cl.
*G06G 7/48* (2006.01)
*C10G 25/00* (2006.01)

(52) U.S. Cl.
CPC ................... *C10G 25/003* (2013.01)

(58) Field of Classification Search
CPC .................................................. C10G 25/003

USPC ............................................................ 703/12
See application file for complete search history.

(56) References Cited

U.S. PATENT DOCUMENTS

| | | | | |
|---|---|---|---|---|
| 6,531,103 B1 * | 3/2003 | Hakka et al. | | 423/242.2 |
| 7,094,333 B2 * | 8/2006 | Yang et al. | | 208/250 |
| 7,435,337 B2 * | 10/2008 | Thomas et al. | | 208/213 |
| 2003/0163013 A1 * | 8/2003 | Yang et al. | | 585/823 |

OTHER PUBLICATIONS

Babich et al.: Science and technology of novel processes for deep desulfurization of oil refinery streams: a review; Fuel 82 (2003) 607-631.*
Gol'dfarb et al.: Synthesis and Some Reactions of Sulfides of the Thiophene Series: XIV. The Action of Bromine and N-Bromosuecinimide on some Chelates of Mercaptoaldimines of the Thiophene Series; Khimiya Geterotsiklicheskikh Soedinenii; 1966; pp. 799-803.*

(Continued)

*Primary Examiner* — Hugh Jones
(74) *Attorney, Agent, or Firm* — Morgan, Lewis & Bockius LLP; Jeffry S. Mann (57) ABSTRACT

A method for predicting selective performance of an adsorbent is disclosed. The adsorbent is selected from a list of metals and/or metal cations for use in removing contaminants as thiophene derivatives in hydrocarbon feed. The metals or metal cations are identified from a list having a positive value for $E_{rel}$, wherein the metal or metal cation having the largest value for $E_{rel}$ is the most selective adsorbent.

4 Claims, 4 Drawing Sheets

(56) References Cited

OTHER PUBLICATIONS

Kagami: Advances in HDS catalysts design—Relation between catalyst structure and feed composition PhD thesis; ter verkrijging van de graad van doctor aan de Technische Universiteit Delft, op gezag van de Rector Magnificus prof. dr. ir. J.T. Fokkema, voorzitter van het College voor Promoties,ISBN: 4-9903244-0-4; 2006; 152 pages.*

Kilanowski et al.; Hydrodesulfurization of Thiophene, Benzothiophene, dibenzothiophene and related compunds catalyzed by sulfided CoO—MoO3 low pressure reactivity studies; J. Catalysis; V. 55, No. 2; 1978; p. 129.*

Kishan et al.: Realistic surface science models of hydrodesulfurization catalysts on planar thin-film supports: the role of chelating agents in the preparation of CoW/SiO2 catalysts; Topics in Catalysis vol. 29, Nos. 3-4; 2004; 103-110.*

Liu et al.: Evidence for Facile and Selective Desulfurization: The Reactions of 2,5- Dihydrothiophene on Mo( 110); J. Am. Chem. SOC 1991, 113, 820-826.*

Natarajan et al: Iron(II), Cobalt(III), Nickel(II) and Copper(II) Chelates of Furan and Thiophene Azo-Oximes; Transition Met. Chem. 9, 18-22 (1984).*

Nehlsen: Developing Clean Fuels: Novel Techniques for Desulfurization PhD Thesis; A Dissertation Presented to the Faculty of Princeton University in Candidacy for the Degree of Doctor of Philosophy; 2005; 145 pages.*

Sakanishi et al; Adsorptive Removal of Sulfur Compounds From Naphtha Fractions by Using Carbon Adsorbents; Prepr. Pap.-Am. Chem. Soc., Div. Fuel Chem. 2003, 48(2), pp. 524-525. Shan et al.: Cu—Ce Bimetal Ion-Exchanged Y Zeolites for Selective Adsorption of Thiophenic Sulfur; Energy & Fuels 2008, 22, 3955-3959.*

Song et al.: Desulfurization; chapter in Encyclopedia of Chemical Processing DOI: 10.1081/E-ECHP-120007732; Taylor & Francis; pp. 651-661; 2006.*

Sripada: Metal Ion Containing Liquid Chromatographic Stationary Phases for the Analysis of Polycyclic Aromatic Sulfur Heterocycles in Fossil Fuels; Inaugural-Dissertation zur Erlangung des Dok. Naturwissenschaften Fachbereich Chemie Pharmazie Mathemathisch-Naturwissenschaftlichen Fakultät Westfälischen Wilhelms-Universität Münster; 2005; 110 pages.*

Steiner: Kinetic and deactivation studies of hydrodesulfurization catalysts; PhD Thesis; Norwegian University of Science and Technology; 2002; 166 pages.*

Zhou et al.; Liquid-Phase Adsorption of Multi-Ring Thiophenic Sulfur Compounds on Carbon Materials with Different Surface Properties; J. Phys. Chem. B 2006, 110, 4699-4707.*

Dai et al.: Desulfurization of transportation fuels targeting at removal of thiophene/benzothiophene; Fuel Processing Technology 89 (2008) 749-755.*

Shan et al.: Cu—Ce Bimetal Ion-Exchanged Y Zeolites for Selective Adsorption of Thiophenic Sulfur; Energy & Fuels 2008, 22, 3955-3959.*

Laborde-Boutet et al: Selectivity of Thiophene/Toluene Competitive Adsorptions onto NaY and NaX Zeolites; Ind. Eng. Chem. Res. 2006, 45, 6758-6764.*

Schapira et al.: Prediction of the binding energy for small molecules, peptides and proteins; Journal of Molecular Recognition; J. Mol. Recognit. 1999;12:177-190.*

* cited by examiner

METHOD FOR PREDICTING ADSORBENT PERFORMANCE

CROSS-REFERENCE TO RELATED APPLICATIONS

This application claims under 35 USC 119(e) the benefit of U.S. Provisional Application No. 61/450,780, filed Mar. 9, 2011, which is incorporated herein by reference in its entirety for all purposes.

FIELD

The invention relates to a method for desulfurizing hydrocarbons, particularly desulfurizing fuel bases for vacuum gas oils, diesel, and kerosene. In one embodiment, the invention relates to the desulfurization of fuel bases containing thiophene derivatives.

BACKGROUND

One of the major challenges facing petroleum refiners today is the ultra-deep desulfurization of diesel, which requires that sulfur levels be reduced to less than 10 ppm. While the concentrations of thiophenes and, to a lesser extent, benzothiophenes can be reduced to the required levels by catalytic hydrodesulfurization, removal of sulfur from 4,6-dialkyl dibenzothiophenes to a similar extent is extremely difficult because the alkyl groups inhibit access to the sulfur atom. A further complication is that the hydrogen demand for removing sulfur from dialkyl dibenzothiophenes is greater than that from other sulfur-containing molecules because one of the benzene rings must first undergo hydrogenation before desulfurization can occur. Furthermore, at the high hydrogen pressures required for desulfurization of dialkyl dibenzothiophenes, some of the aromatic compounds present in diesel also undergo hydrogenation, further raising the overall hydrogen required for deep desulfurization.

A possible alternative to hydrodesulfurization is selective adsorption of thiophene derivatives on a solid adsorbent. The most promising of materials that have been explored to date are based on cation-exchanged zeolites and metals, metal halides, other metal salts supported on activated carbon (AC). Metal cations such as $Na^+$, $K^+$, $Ag^+$, $Ni^{2+}$, $Cu^{2+}$, $Zn^{2+}$, $Pd^{2+}$, $Fe^{3+}$, $Ce^{3+}$ have been considered as adsorption centers. Adsorbents based on activated carbon have generally been found to exhibit higher adsorption capacities than those based on zeolites, and it has been reported that the adsorption capacity for benzothiophene and dibenzothiophene follows the order $Ag^+/AC>Ni^{2+}/AC>Cu^{2+}/AC>Zn^{2+}/AC>AC>Fe^{3+}/AC$. Amongst zeolitic materials, $Cu^+/Y$ has been reported to be the most effective. What has not been addressed in these studies is the relative strength of binding of arenes such as naphthalene, anthracene, and their derivative compared to benzothiophene, dibenzothiophene, and other thiophene derivatives. This is an important issue, since liquid fuels, such as hydrotreated diesel contains much higher concentrations of arenes (often more than 10%) than of thiophene derivatives (often less than 50 ppm) following deep hydro-desulfurization.

There is still a need for improved methods to select metal atoms or cations that will preferentially bind, for example, dimethyl dibenzothiophene with respect to anthracene or naphthalene. The invention relates to a method to predict and select metal adsorption centers for preferential adsorption of thiophene derivatives in the presence of arenes.

SUMMARY

In one aspect, the invention relates to a method for predicting selective performance of an adsorbent from a list of metals and/or metal cations for use in removing contaminants as thiophene derivatives in hydrocarbon feed. The method comprises the steps of: identifying the thiophene derivatives to be removed from the hydrocarbon feed as contaminants; identifying aromatics in the hydrocarbon feed having similar aromaticity corresponding to the identified thiophene derivatives; computing interaction of each of the metal or metal cation on the list with each of the thiophene derivatives as first binding energy; computing interaction of the metal or metal cation with one or more aromatic compounds having similar aromaticity as second binding energy; subtracting the first binding energy from the second binding energy to get a value of relative energy $E_{rel}$ (where $E_{rel}$ is difference in binding energy of aromatics and thiophene derivatives), for each metal or metal cation and each identified pair of thiophene derivative and corresponding aromatic compound; and identifying the metals or metal cations from the list having a positive value for $E_{rel}$, wherein the metal or metal cation having the largest value for $E_{rel}$ is the most selective adsorbent.

In another aspect, a method of tailoring an adsorbent to a hydrocarbon feed for removing contaminants as thiophene derivatives is disclosed. The method comprises: identifying one or more thiophene derivatives in the hydrocarbon feed; identifying aromatics in the hydrocarbon feed having similar aromaticity corresponding to the identified thiophene derivatives; identifying a plurality of metal or metal cations for consideration as candidates for the adsorbent; computing interaction of each the identified metals or metal cations with each of the identified thiophene derivatives as first binding energy; computing interaction of each the identified metals or metal cations with each of the identified aromatics as second binding energy; subtracting the first binding energy from the second binding energy to compute difference between the second binding energy and the first binding energy as $E_{rel}$; and identifying at least a metal or metal cation having a positive value for $E_{rel}$.

In yet another aspect, a method of enhancing selective performance of an adsorbent for a metal or metal cation in removing contaminants as thiophene derivatives in a hydrocarbon feed is disclosed. The method comprises: providing a list of compounds for use as chelating agents for the metal or metal cation to form chelated metals or chelated metal cations; identifying the thiophene derivatives to be removed from the hydrocarbon feed as contaminants; identifying aromatics in the hydrocarbon feed having similar aromaticity corresponding to the identified thiophene derivatives; computing interaction of each of the chelated metals or chelated metal cations on the list with each of the thiophene derivatives as first binding energy; computing interaction of each of the chelated metals or chelated metal cations with the at least an aromatic compound having similar aromaticity as second binding energy; subtracting the first binding energy from the second binding energy to get a value $E_{rel}$ for each chelated metal or chelated metal cation and each identified pair of thiophene derivative and corresponding aromatic compound; and identifying the chelated metals or chelated metal cations having a positive value for $E_{rel}$, wherein the chelated metal or chelated metal cation having the largest value for $E_{rel}$ is the most selective adsorbent.

DETAILED DESCRIPTION

In one embodiment, the invention relates to a method to predict the selective performance of metals and/or metal cations in the removal of thiophene derivatives from hydrocarbon products, e.g., vacuum gas oils, kerosene and diesel fuels, particularly hydrocarbon fuels containing thiophene derivatives.

In one embodiment, the selective performance of an adsorbent can be predicted by first carrying out quantum chemical calculations of the binding energy of naphthalene, anthracene, benzothiophene, dibenzothiophene, and 4,6-dimethyl dibenzothiophene for a variety of metal atoms and cations. In the next step, the results are analyzed in order to determine the principles by which to select adsorption centers exhibiting preferential binding of the thiopene derivative over arenes in the hydrocarbon feed having similar aromaticity. What was found is that thiophene derivatives are bound preferentially to arenes on metal cations having low Lewis acidity and high chemical hardness. The difference in the binding energies between arene and thiophene derivative can be optimized by controlling the effective charge on the cation.

In one embodiment, the calculations can be performed at the DFT/B3LYP (DFT: density functional theory; B3LYP: Becke 3-Parameter) level using a Gaussian 03 package. Metal atoms and cations can be described using the LANL2DZ (Los Alamos National Laboratory 2-double-z (density functional theory)) basis set, whereas ligands (CO, $N(CH_3)_3$, $P(CH_3)_3$, pyridine) and adsorbates (naphthalene (NPT), anthracene (ANT), benzothiophene (BTP), dibenzothiophene (DBT) 4,6-dimethyl dibenzothiophene (DMDBT)) can be described using cc-pVQZ basis sets (cc-pVQZ: correlation-consistent polarized valence quadruple zeta).

The partial atomic charges of adsorbates can be obtained using RESP (Restrained Electrostatic Potential) in Antechamber tools of Amber 11. The strength of metal atoms or cation interaction with adsorbates can be interpreted in terms of the electron affinity, $\chi$, and hardness, $\eta$, of the interacting species, and by the extent of orbital overlap between the interacting species. The electron affinity and chemical hardness can be calculated from the following relationships:

$$\chi = -\frac{(\varepsilon_{HOMO} + \varepsilon_{LUMO})}{2}$$

$$\eta = \frac{(\varepsilon_{HOMO} - \varepsilon_{LUMO})}{2}$$

In the above equations, and represent the energy levels of the highest occupied molecular orbital and the lowest unoccupied molecular orbital, respectively. Electron density surfaces of the HOMO (Highest Occupied Molecular Orbital) and LUMO (Lowest Unoccupied Molecular Orbital) states can be obtained using VESTA. All the HOMO and LUMO electron density surfaces are reported for an isovalue 0.02 (electrons/Å$^3$). The blue and brown colors of the isosurfaces represent lobes of positive and negative phase wave function, respectively. The extent of overlap between the electron density isosurfaces associated with the metal and the adsorbate provides information about the character of the metal-adsorbate bonding. Constructive overlap between metal and adsorbate orbitals (overlap of orbital lobes with similar phase) is characteristic of covalent bonds or pi back bonding. For the systems examined, this condition was observed for transition metals with partially filled d orbitals and low chemical hardness (e.g., $Rh^{3+}$, $Pd^{2+}$, $Ni^0(LS)$). A negligible overlap between metal and ligand orbitals is characteristic of charge controlled interactions, which can be strong or weak depending on the charge of the interacting species.

EXAMPLES

The following illustrative examples are intended to be non-limiting. In the examples, a number of adsorbates were considered. Values of electronegativity $\chi$ and chemical hardness $\eta$ for each of the adsorbates considered are listed in Table 1.

TABLE 1

| Adsorbate | Electronegativity, $\chi$ (eV) | Chemical Hardness, $\eta$ (eV) |
|---|---|---|
| BTP | 0.1314 | 0.0945 |
| NPT | 0.1372 | 0.0879 |
| 4,6-DMDBT | 0.1309 | 0.0870 |
| DBT | 0.1362 | 0.0864 |
| ANT | 0.1388 | 0.0651 |

The $\chi$ values or the HOMO-LUMO gap calculated from DFT studies and known semi empirical methods differ. However, the values from semi empirical calculations are in agreement with quantum chemical calculations. The results (NPT and ANT; 4.78 and 3.54 eV) are in agreement with the $\eta$ values reported in the literature. The values of $\chi$ for all of the adsorbates lie between 0.13 and 0.14 eV. Since strong Lewis acids are characterized by $\chi \geq 1.0$ eV, the arene and thiophenes considered here are relatively weak Lewis acids, and correspondingly relative strong Lewis bases. A greater variation occurs in the values of $\eta$, arenes (NPT and ANT) being somewhat softer Lewis bases than thiophenes (BTP, DBT, and DMDBT). As observed, with increasing ring number, both the arenes and thiophenes become softer Lewis bases, reflecting the increase in molecular polarizability with increasing aromaticity of the system.

The quantum calculations also show that the electronic charge on the sulfur atom in the thiophene ring increases with increasing number of benzene rings attached to the thiophene ring and the presence of electron-donating methyl groups on the benzene rings. The charge on the S atom of thiophene (TPH) is positive (qs=0.038|e|) but becomes negative for all benzothiophene and dibenzothiophene derivatives, decreasing in the order BTP (−0.039|e|)>DBT (−0.136|e|)>4,6-DMDBT (−0.158|e|). It is noted that the carbon atoms have larger negative partial charges than the sulfur atom in case of BTP and DBT, but the opposite is true in the case of DMDBT due to presence of electron donating methyl groups.

Table 2 lists the values of electronegativity $\chi$ and chemical hardness $\eta$ for each of the metal atoms or cations investigated and the absolute binding and relative energies for the interactions of these adsorbents with NPT and BTP.

TABLE 2

| Metal | Chemical hardness $\eta$ (eV) | Electro-negativity $\chi$ (eV) | $E_{bind}$ (M-NPT), kJ/mol | $E_{bind}$ (M-BTP), kJ/mol | $E_{rel}$, kJ/mol |
|---|---|---|---|---|---|
| $Rh^{3+}$(LS) | 0.12 | 2.96 | −2609.5 | −2573.4 | −36.07 |
| $Zn^{2+}$ | 0.6 | 2.06 | −2553.5 | −2553.6 | 0.1 |
| $Pd^{2+}$(LS) | 0.05 | 2.03 | −1229 | −1225.7 | −3.28 |
| $Cu^{2+}$ | 0.45 | 1.93 | −1085.4 | −1079.8 | −5.6 |
| $Co^{2+}$(HS) | 0.37 | 1.78 | −845.42 | −833.39 | −12.03 |
| $Hg^{2+}$ | 0.44 | 1.94 | −715 | −699.7 | −15.3 |
| $Au^{+1}$ | 0.17 | 1.06 | −294.29 | −245.69 | −48.6 |
| $Cu^{+1}$ | 0.19 | 0.95 | −233.67 | −235.29 | 1.62 |
| $Ni^0$(LS) | 0.06 | 0.3 | −202.99 | −157.13 | −45.86 |
| $Ag^{+1}$ | 0.26 | 1.01 | −165.4 | −168.4 | 3 |
| $Pd^0$ | 0.09 | 0.26 | −98.6 | −76.66 | −21.94 |
| $Au^0$ | 0.22 | 0.27 | −14.67 | −25.04 | 10.37 |
| $Cu^0$ | 0.17 | 0.21 | −21.56 | −13.62 | −7.94 |
| $Ag^0$ | 0.17 | 0.21 | −3.18 | −3.12 | −0.06 |
| $Hg^0$ | 0.25 | 0.22 | −0.0289 | −0.032 | 0.0031 |

Figure 1:
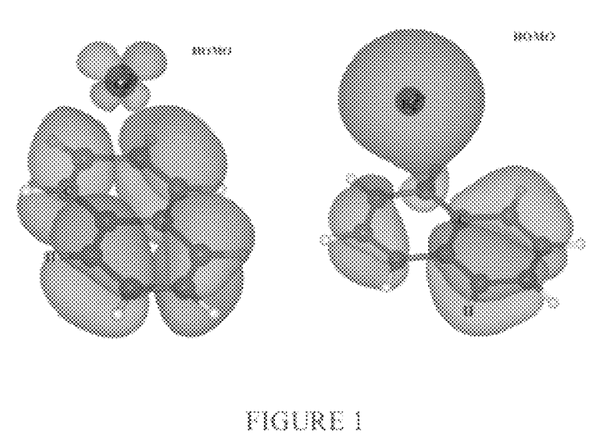
FIG. 1 shows the HOMO electron density surfaces for the interactions of $Cu^{2+}$ and $Hg^{2+}$ with naphthalene.

In general, the strength of adsorbent-adsorbate interaction decreases with decreasing strength of Lewis acidity ($\chi$) and for equivalent, or nearly equivalent, values of $\chi$ with a decreasing value of $\eta$. Thus, for $\chi_1 \approx \chi_2$ and $\eta_1 < \eta_2$, the strength of adsorbate binding will be higher for metal 1 than metal 2, i.e., $E_1 < E_2$. This trend is exactly the trend that would be predicted by Pearson's rules for the interactions of acids and bases. However, a number of anomalies to this trend are observed. For example, when $\chi_1 \approx \chi_2$ and $\eta_1 \approx \eta_2$, $E_1 < E_2$, as is the case for $Cu^{2+}$ compared to $Hg^{2+}$. The reason for the higher interaction energy for $Cu^{2+}$ can be ascribed to the degree of constructive overlap between orbitals of the metal and the adsorbate. The $t_{2g}$-type d orbitals of $Cu^{2+}$ interact with a larger fraction of the electron-density surface of NPT than does the s orbital of $Hg^{2+}$, as can be seen in FIG. 1.

Figure 2:
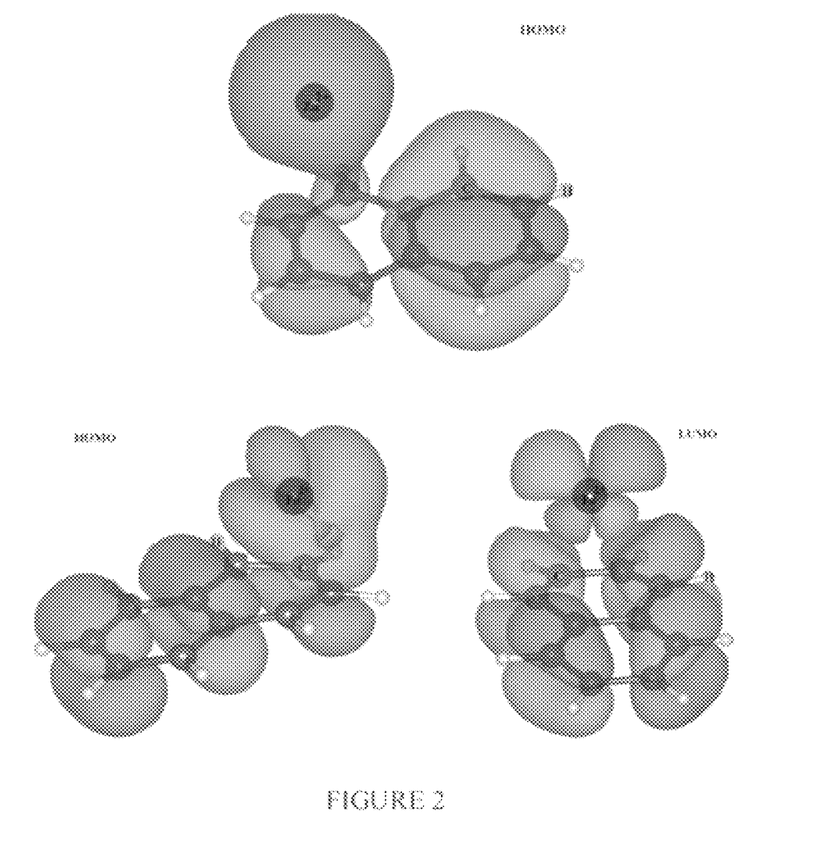
FIG. 2 shows the electron density surfaces for HOMO for the interactions of $Zn^{2+}$ and $Pd^{2+}$ with naphthalene and electron density surfaces for the LUMO for the interaction of $Pd^{2+}$ with naphthalene.

Anomalies exist, as well, for two other cases. The first is when $\chi_1 \approx \chi_2$ and $\eta_1 > \eta_2$, as is the case for $Zn^{2+}$ compared to $Pd^{2+}$. The second is when $\chi_1 < \chi_2$ and $\eta_1 < \eta_2$, as is the case for $Co^{2+}$ compared to $Hg^{2+}$, $Ni^0$ compared to $Ag^+$, $Pd^0$ compared to $Au^0$, and $Cu^0$ compared to $Au^0$. In each of these two cases, the higher binding energy occurs for the first member of the pair. The explanations of the anomalies for the two cases are different. For the first case, exemplified by $Pd^{2+}$ and $Zn^{2+}$, $Pd^{2+}$ has a lower chemical hardness than $Zn^{2+}$ and hence should have better overlap of metal-ligand orbitals. This is, indeed, observed in the electron density plot of the HOMO of the $Pd^{2+}$-NPT complex (see FIG. 2). However, in the electron density plot of the LUMO, this overlap is offset as a consequence of the overlap of orbitals lobes of opposite phases. The overlap causes a reduction in the overall pi-back bonding in this case. For this reason $Pd^{2+}$ binding energy is lower than that for $Zn^{2+}$. $Zn^{2+}$ does not have orbital overlap with NPT, due to its high chemical hardness and consequently only charge-controlled interactions with NPT occur.

For the second case, the first metal atom or cation is less electronegative than the second one, but softer.

Figure 3:
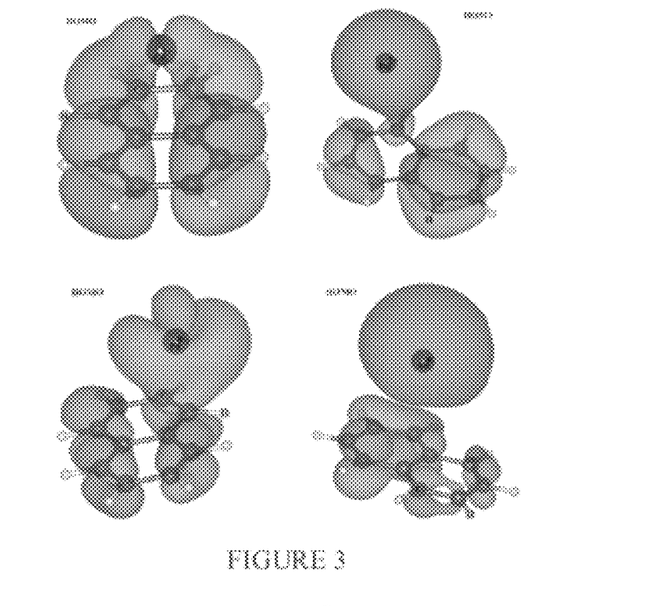
FIG. 3 shows the electron density surfaces the HOMO for the interactions of $Co^{2+}$, $Hg^{2+}$, $Pd^0$, and $Au^0$ with naphthalene.

The higher binding energy for the first metal atom or cation is attributable to the greater orbital overlap between the atomic orbitals of the metal atom (cation), and the molecular orbitals of NPT. This effect is seen in the electron density plot shown in FIG. 3 for the HOMO of $Co^{2+}$ compared to $Hg^{2+}$, and $Pd^0$ compared to $Au^0$. Thus, the extended rules for anticipating strong metal NPT interactions are high Lewis acidity ($\chi$), low chemical hardness ($\eta$), and a high degree of overlap between the orbitals of the metal atom (or cation) and the adsorbate. While these rules were inferred from an examination of the binding energies for NPT, a similar pattern can also be deduced for BTP.

Inspection of Table 2 reveals a second interesting feature. While the Lewis acidities and chemical hardnesses of NPT and BTP are very similar, the binding energies for these two molecules can differ considerably. Therefore, the small differences in the values of $\chi$ and $\eta$ for BTP and NPT cannot account for the differences between the metal-adsorbate binding energies for NPT and BTP, as listed in Table 2.

Figure 4:
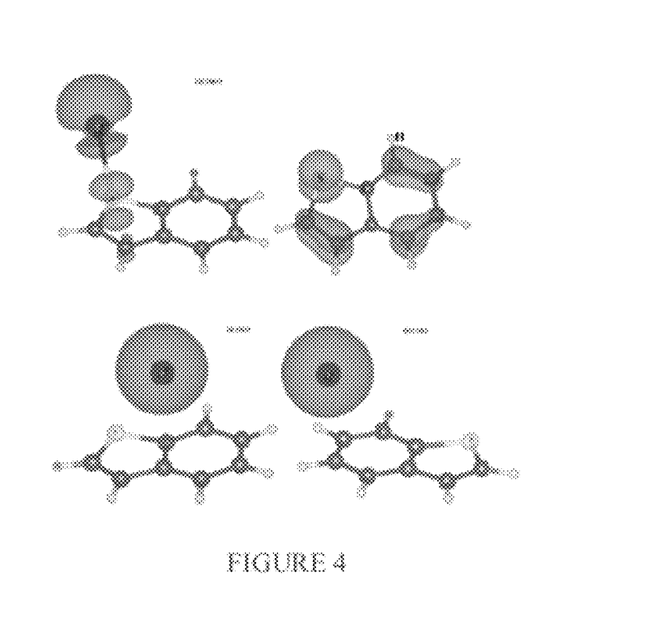
FIG. 4 shows the electron density surfaces of the HOMO (0.06 eV/Å$^3$) for interaction with $Au^0$, $Hg^0$, $Cu^0$, and $Ag^0$ with naphthene.

Stronger binding for BTP relative to NPT (e.g. $E_{rel} > 0$, where $E_{rel}$ is difference in binding energy of NPT and BTP complex) occurs when the metal atom or cation has a high chemical hardness relative to that of metal atom or cations of comparable Lewis acidity. This point is nicely illustrated by comparing the values of $E_{rel}$ for $Au^0$ and $Pd^0$, $Au^0$ and $Au^{-1}$, $Ag^+$ and $Au^+$ or $Cu^+$ and $Au^+$ for which the first member of the pair exhibits a higher binding energy for BTP than NPT. The difference between the binding energy of the BTP and NPT also increases when the HOMO of the metal atom (or cation) is similar in shape to the p orbitals of sulfur. The point is best illustrated by comparing $Au^0$ and $Hg^0$, for which $\eta_2 > \eta_1$. The first member of the pair has a higher value of $E_{rel}$, due to presence of $e_g$-type d orbitals that are shaped similarly to the p orbitals of S (see FIG. 4). The reason why the difference in binding energies for BTP versus NPT is so large for $Au^0$ relative to that for $Cu^0$ and $Ag^0$ is that the d orbitals of these latter metals do not participate in the binding to S, as can be seen from FIG. 4. Interestingly, the main group elements $Li^+$, $K^+$ and $Mg^{2+}$ in Table 3 have lower binding energies and negative values Erel compared to transition metals of similar $\chi$. These differences are probably due to the absence of d orbitals for these cations. Thus, metals with high $\eta$, low $\chi$, and eg-type d orbitals are the best candidates for strong binding to the S atom of thiophenes.

TABLE 3

Binding energies, kJ/mol of $Li^+$, $K^+$ and $Mg^{2+}$.

| Metal | Electro-negativity, $\chi$ (eV) | Chemical Hardness, $\eta$ (eV) | $E_{bind}$ (M-NPT) (kJ/mol) | $E_{bind}$ (M-BTP) (kJ/mol) | $E_{rel}$, (kJ/mol) |
|---|---|---|---|---|---|
| $Li^+$ | 1.30 | 1.05 | −163.69 | −148.52 | −15.17 |
| $K^+$ | 0.60 | 0.39 | −68.62 | −63.09 | −5.53 |
| $Mg^{2+}$ | 0.26 | 0.26 | −531.83 | −499.85 | −31.98 |

The relationship between the binding energies of thiophene derivatives and arenes with the same number of aromatic rings was extended to DBT and ANT, and to DMDBT and ANT. The results of these calculations are presented in Table 4, showing the binding energy of Au in various oxidation states with adsorbates.

TABLE 4

| Metal | $q_M$ | $E_{bind}$(NPT) | $E_{bind}$(BTP) | $E_{bind}$(ANT) | $E_{bind}$(DBT) | $E_{bind}$ (4,6-DMDBT) |
|---|---|---|---|---|---|---|
| $Au^{-1}$ | −1 | −34.73 | −29.86 | — | — | — |
| $Au^0$ | 0 | −14.67 | −25.04 | −16.38 | −28.47 | −32.50 |
| $[Au(P(CH_3)_3)]^+$ | 0.56 | −136.67 | −149.47 | −140.97 | — | −165.20 |
| $[Au(N(CH_3)_3)]^+$ | 0.68 | −192.36 | −194.19 | −203.59 | −224.17 | −229.19 |
| $[Au(NC_5H_5)]^+$ | 0.70 | −201.09 | −219.10 | −211.98 | — | −237.19 |
| $[Au(CO)]^+$ | 0.88 | −252.83 | −262.71 | −392.09 | — | −412.86 |
| $Au^+$ | +1 | −294.29 | −245.69 | −319.90 | −320.02 | −334.90 |
| $Cu^+$ | +1 | −233.67 | −235.29 | −249.64 | −220.28 | −254.87 |
| $Ag^+$ | +1 | −165.40 | −168.40 | −183.80 | −173.70 | −195.01 |
| $Cu^{2+}$ | +2 | −1085.40 | −1079.80 | −1223.80 | — | −1182.38 |
| $Mg^{2+}$ | +2 | −531.83 | −499.85 | −535.35 | — | −514.29 |
| $K^+$ | +1 | −68.62 | −63.09 | −74.66 | — | −75.44 |

It is observed first of all that for $Au^0$ the binding energy for ANT is slightly higher than that of NPT. Since ANT and NPT have very similar Lewis acidities, the observed preference for binding ANT is due to its lower chemical hardness, which enhances the ability of this molecule to have better orbital overlap with $Au^0$. The same effect accounts for the increasing binding strength as one progresses from BTP to DBT to DMDBT. Similar patterns in the absolute binding energies of ANT compared to NPT and the progressively stronger binding energy of the thiophene derivatives with increasing number of benzene rings and methyl groups can be seen for $Au^+$, except that the differences in all cases are larger. This is very likely a consequence of the higher Lewis acidity of $Au^+$ compared to $Au^0$.

Table 4 also shows that for a given oxidation state of Au, the difference between the binding energies for arene versus the corresponding thiophene derivative increases (becomes more positive) with increasing negative charge on the S atom of the thiophene derivative. This effect is particularly dramatic for interactions with $Au^+$, for which the difference in binding energies is negative for NPT compared to BTP, is nearly zero for ANT compared to DBT, and is positive for ANT compared to DMDBT. What these trends mean is that $Au^0$ will preferentially interact with all thiophene derivatives and that $Au^+$ will interact preferentially with DMDBT relative to NPT, ANT, BTP, or DBT. Similar trends are observed for $Cu^+$ and $Ag^+$, which show higher binding energy for BTP and DMDBT than NPT and ANT but lower binding energy for DBT than ANT.

A higher relative binding energy for DMDBT versus ANT, but not for DBT versus ANT or BTP versus NPT, was also observed for other metals with intermediate Lewis acidity $Cu^+$, $Ag^+$ and $K^+$. However, this effect was not seen for more Lewis acidic metals, such as $Cu^{2+}$ and $Mg^{2+}$. DMDBT is an exception because the methyl side groups cause the negative charge on sulfur to be larger than that on the carbon atoms, resulting in a larger binding energy for DMDBT than ANT with metals of intermediate Lewis acidity. Additional selectivity towards the coordination of thiophene derivatives relative to the corresponding arenes can be achieved by tuning the charge on Au by allowing $Au^+$ to interact with a single ligand.

Figure 5:
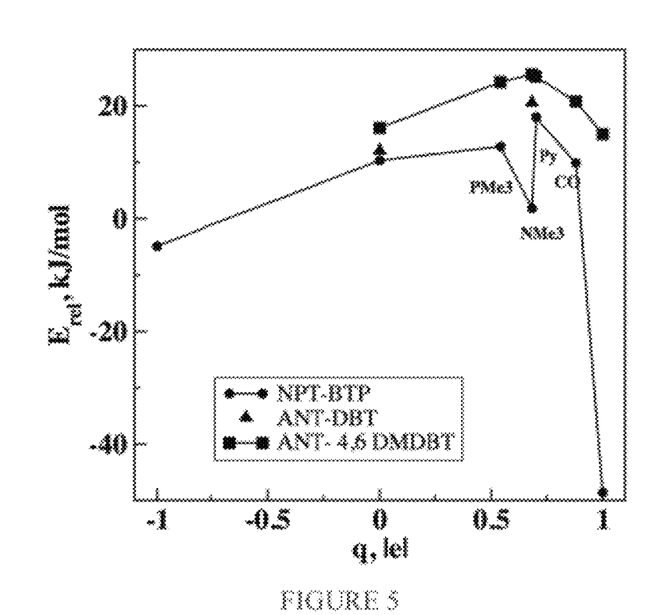
FIG. 5 is a plot of $E_{rel}$, the difference between the binding energy of arenes and thiophene derivatives, as a function of effective partial charge on Au.

Table 4 and FIG. 5 show the difference between the binding energies of arenes and thiophene derivatives, $E_{rel}$, having the same number of aromatic rings. $E_{rel}$ becomes more positive going from $Au^0$ to $Au(P(CH_3)_3)^+$($q_{eff}$(Au)= 0.54|e|), less positive for $Au(N(CH_3)_3)^+$($q_{eff}$(Au)=0.67|e|), becomes strongly positive for $Au(NC_5H_5)^+$($q_{eff}$(Au)= 0.70|e|), becomes slightly less positive for $Au(CO)^+$($q_{eff}$(Au)=0.88|e|), and then becomes strongly negative for $Au^+$.

Figure 6:
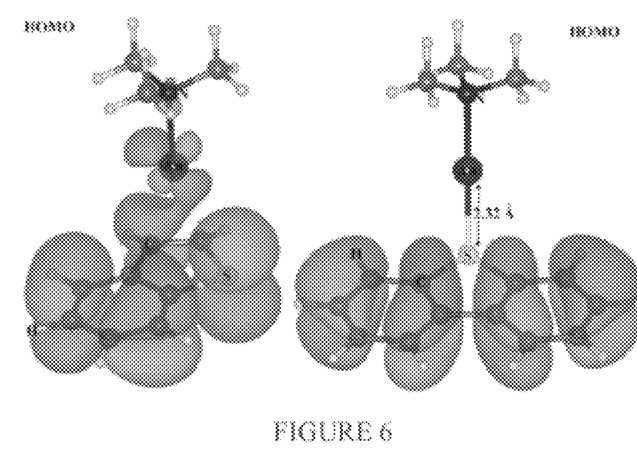
FIG. 6 shows the electron density surfaces of the HOMO for $[Au(N(CH_3)_3)]^+$ complexes with benzothiophene and dibenzothiophene.

The decrease in the difference of binding energies between NPT and BTP for $Au(N(CH_3)_3)^+$ is due to the interaction of $Au(N(CH_3)_3)^+$ with the $C_7$ of BTP instead of the sulfur atom which reduces selectivity for BTP, as shown in the HOMO LUMO electron density surfaces in FIG. 6. By contrast, the difference in binding energies for ANT compared to DMDBT is always positive but reaches a maximum for $Au(P(CH_3)_3)^+$ and $Au(N(CH_3)_3)^+$.

Figure 7:
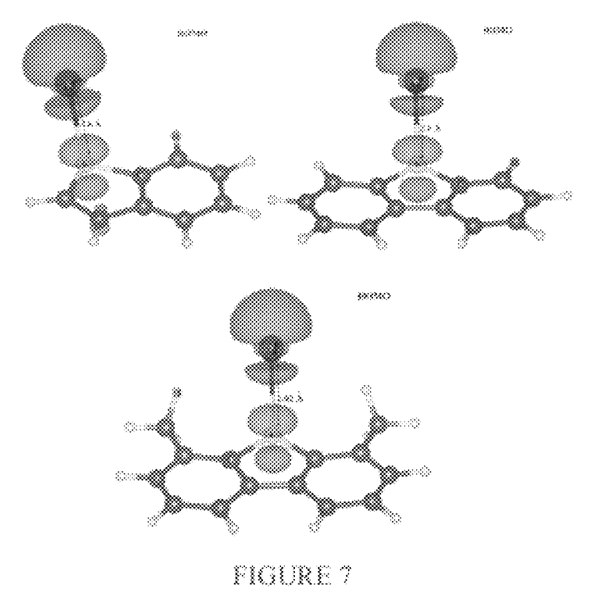
FIG. 7 shows the electron density surfaces of the HOMO ((0.06 eV/Å$^3$) for $Au^0$ interactions with benzothiophene, dibenzothiophene, and 4,6-dimethyl dibenzothiophene.

It should be noted that the absolute binding energies for all substrates increase monotonically as the charge on Au increases from 0 to +1, consistent with the progressively higher Lewis acidity of the metal. The variation in the difference in binding energies between ANT and DBT follows a pattern very similar to that seen for the difference in binding energies between ANT and DMDBT, but the magnitude of the difference is smaller. An important observation is that $Au^0$ and $[AuL]^+$ are unique in that these species interact selectively with the S atom of all the thiophenes examined FIG. 7 clearly shows this to be the case for $Au^0$ complexes.

The results demonstrate that preferential adsorption of thiophene derivatives over arenes is achieved by using a metal cation that is a weak Lewis acid and with a high chemical hardness and atomic projected orbitals, having p character and, hence, good overlap well the p orbitals of sulfur. By contrast, soft Lewis acids increase the degree of i-back bonding, leading to preferred bonding of arenes. Zero valent Au meets the specifications for selective preferential binding of thiophene derivatives versus arenes containing the same number of aromatic rings. On the other hand, $Au^+$ does not meet the specifications, except for the case of DMDBT binding versus ANT binding. However, when an electron-donating ligand is allowed to interact with Au+, the effective charge on the cation is reduced.

At an effective charge of about 0.8|e|, preferential adsorption of benzothiphene over naphthalene is observed, as well as preferential binding of dibenzothiophene and dimethyl diobenzothiophene over anthracene. This can be achieved using pyridine as the ligand. The analysis of the factors controlling the selective adsorption of thiophene derivative compared to arenes can also explain why $Ag^+$ and $Cu^+$ have been proposed in the literature as good candidates for the deep desulfurization of diesel based on MNDO (MDNO: (modified neglect of diatomic overlap) calculations, showing preferential thiophene over benzene, have, in fact, not proven to be effective for deep desulfurization of commercial diesel.

Figure 8:
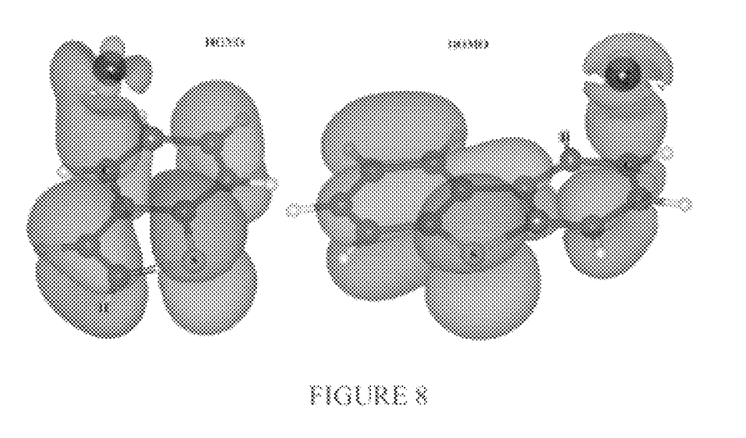
FIG. 8 shows the electron density surfaces of the HOMO for interactions of $Ag^+$ with benzothiophene and dibenzothiophene.

Table 5 shows that while the binding of BTP is stronger than that of NPT for $Ag^+$ and $Cu^+$ as the number of aromatic rings increases, the selectivity observed for BTP versus NPT reverses and now ANT binds more favorably than DBT. A careful analysis of HOMO electron density surfaces (see FIG. 8) of these complexes shows that $Cu^+$ and $Ag^+$ do not interact with the S atom in the DBT and, instead, interact preferentially with the neighboring more basic C atoms. The reversal in the selectivity pattern with increasing number of aromatic rings is attributable to the unpredictable changes in partial atomic charges on the carbon atoms of arenes and thiophenes. By contrast, the negative charge on sulfur increases monotonically with increasing number of arene rings. Since diesel is rich in higher thiophenes, $Cu^+$ and $Ag^+$ are not ideal candidates for deep desulfurization of this fuel

TABLE 5

Binding energy of $Cu^+$ and $Ag^+$ with NPT, BTP, ANT and DBT

| Metal | $E_{bind}$ (M-NPT), kJ/mol | $E_{bind}$ (M-BTP), kJ/mol | $E_{bind}$ (M-ANT), kJ/mol | $E_{bind}$ (M-DBT), kJ/mol |
|---|---|---|---|---|
| $Cu^+$ | −233.67 | −235.29 | −249.64 | −220.28 |
| $Ag^+$ | −165.40 | −168.40 | −183.80 | −173.70 |

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present invention. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items.

This written description uses examples to disclose the invention, including the best mode, and also to enable any person skilled in the art to make and use the invention. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. All citations referred herein are expressly incorporated herein by reference.

The invention claimed is:

1. A method of predicting selective performance of an adsorbent from a list of metals and/or metal cations for use in selectively removing thiophene and thiophene derivatives in a hydrocarbon feed containing aromatics having a similar aromaticity or a same ring number corresponding to the thiophene and thiophene derivatives comprising:
   identifying the thiophene and thiophene derivatives to be removed from the hydrocarbon feed as contaminants;
   identifying aromatics in the hydrocarbon feed having said similar aromaticity or the same ring number corresponding to the identified thiophene and thiophene derivatives;
   computing an interaction of each of the metals and/or metal cations on the list with each of the thiophene and thiophene derivatives as a first binding energy;
   computing an interaction of the metals and/or metal cations with one or more aromatic compounds having said similar aromaticity or the same ring number as a second binding energy;
   subtracting the first binding energy from the second binding energy to get a value $E_{rel}$ for each of the metals and/or metal cations and each identified pair of thiophene and thiophene derivative and corresponding aromatic compound;
   identifying a selective adsorbent from the metals and/or metal cations having a positive value for $E_{rel}$, wherein the metal or metal cation having the largest positive value for $E_{rel}$, is the most selective adsorbent, and contacting said selective adsorbent with the hydrocarbon feed containing thiophene, thiophene derivatives, and other arenes, thereby selectively adsorbing said thiophene and thiophene derivatives.

2. A method of tailoring an adsorbent to a hydrocarbon feed for selectively removing thiophene and thiophene derivatives wherein the hydrocarbon feed contains aromatics having a similar aromaticity or a same ring number corresponding to the thiophene and the thiophene derivatives, comprising the steps of:
   identifying one or more thiophene and thiophene derivatives in the hydrocarbon feed;
   identifying aromatics in the hydrocarbon feed having said similar aromaticity or the same ring number corresponding to the identified thiophene and thiophene derivatives;
   identifying a plurality of metals and/or metal cations for consideration as candidates for the adsorbent;
   computing an interaction of each the identified metals and/or metal cations with each of the identified thiophene and thiophene derivatives as a first binding energy;
   computing an interaction of each the identified metals and/or metal cations with each of the identified aromatics as a second binding energy;
   subtracting the first binding energy from the second binding energy to compute a binding energy difference as $E_{rel}$;
   identifying at least a metal or a metal cation having a positive value for $E_{rel}$, contacting said adsorbent with the hydrocarbon feed containing thiophene, thiophene derivatives, and other arenes, thereby selectively adsorbing said thiophene and thiophene derivatives.

3. The method of claim 2, further comprising selecting the metal or metal cation having the largest positive value of $E_{rel}$ as a component for the adsorbent.

4. A method of enhancing selective performance of an adsorbent comprising at least a metal or a metal cation in selectively removing thiophene and thiophene derivatives in a hydrocarbon feed containing aromatics having a similar aromaticity or a same ring number corresponding to the thiophene and thiophene derivatives, comprising the steps of:
   providing a list of compounds for use as chelating agents for the metal or the metal cation to form chelated metals or chelated metal cations;
   identifying thiophene and thiophene derivatives to be removed from the hydrocarbon feed as contaminants;
   identifying aromatics in the hydrocarbon feed having said similar aromaticity or the same ring number corresponding to the identified thiophene and thiophene derivatives;

computing an interaction of each of the chelated metals or chelated metal cations on the list of compounds with each of the thiophene and thiophene derivatives as a first binding energy;

computing an interaction of each of the chelated metals or chelated metal cations with one or more aromatic compounds having said similar aromaticity or the same ring number as a second binding energy;

subtracting the first binding energy from the second binding energy to get a value $E_{rel}$ for each of the chelated metals or chelated metal cations and each identified pair of thiophene and thiophene derivative and corresponding aromatic compound;

identifying a selective adsorbent from the chelated metals or chelated metal cations having a positive value for $E_{rel}$, wherein the chelated metal or chelated metal cation having the largest positive value for $E_{rel}$ is the most selective adsorbent, and contacting said selective adsorbent with a hydrocarbon feed containing thiophene, thiophene derivatives, and other arenes, thereby selectively adsorbing said thiophene and thiophene derivatives.

* * * * *